(12) United States Patent
Walker et al.

(10) Patent No.: US 9,275,189 B2
(45) Date of Patent: Mar. 1, 2016

(54) SCAN PARAMETER POLICY

(75) Inventors: Matthew J. Walker, Willoughby, OH (US); Mark E. Olszewski, Solon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 915 days.

(21) Appl. No.: 13/503,173

(22) PCT Filed: Oct. 19, 2010

(86) PCT No.: PCT/IB2010/054732
§ 371 (c)(1),
(2), (4) Date: Apr. 20, 2012

(87) PCT Pub. No.: WO2011/048547
PCT Pub. Date: Apr. 28, 2011

(65) Prior Publication Data
US 2012/0213326 A1  Aug. 23, 2012

Related U.S. Application Data

(60) Provisional application No. 61/253,880, filed on Oct. 22, 2009.

(51) Int. Cl.
*A61B 6/00* (2006.01)
*G06F 19/00* (2011.01)
*A61B 6/03* (2006.01)
*A61B 6/10* (2006.01)

(52) U.S. Cl.
CPC ............ *G06F 19/3406* (2013.01); *A61B 6/032* (2013.01); *A61B 6/542* (2013.01); *A61B 6/545* (2013.01); *A61B 6/107* (2013.01)

(58) Field of Classification Search
CPC .......... A61B 6/00; A61B 6/032; G01N 23/00; G01N 23/046; G01N 23/06; G06T 2211/00; G06T 2211/40
USPC ...................................................... 378/4, 901
See application file for complete search history.

(56) References Cited

U.S. PATENT DOCUMENTS

| 7,254,623 | B1 | 8/2007 | Toth |
| 7,490,987 | B2 | 2/2009 | Busch |
| 7,620,142 | B1 | 11/2009 | Toth |
| 7,925,519 | B2* | 4/2011 | Greene .............................. 705/2 |
| 8,000,510 | B2* | 8/2011 | Boeing et al. ................. 382/128 |
| 2008/0015892 | A1 | 1/2008 | Gowdy et al. |
| 2008/0103834 | A1 | 5/2008 | Reiner |
| 2008/0240336 | A1 | 10/2008 | Miyazaki et al. |
| 2009/0074143 | A1 | 3/2009 | Tsukagoshi et al. |

* cited by examiner

*Primary Examiner* — Jurie Yun

(57) ABSTRACT

A computing apparatus includes a processor (212) that evaluates at least one scan parameter of a scan protocol selected for scanning a subject with an imaging system (102) based on a corresponding scan parameter policy and generates a signal indicative of whether the scan parameter satisfies the scan parameter policy.

63 Claims, 8 Drawing Sheets

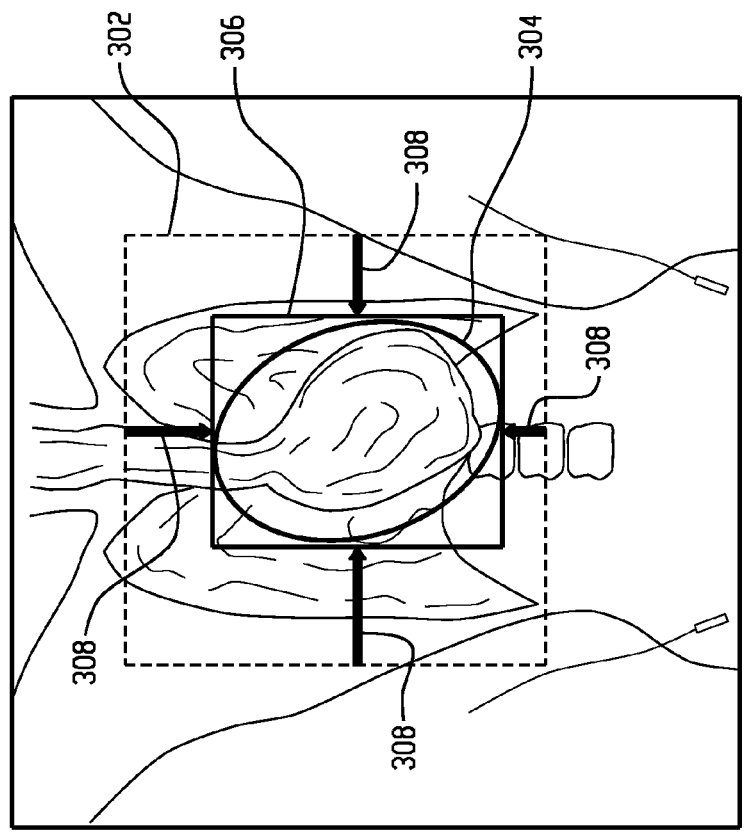
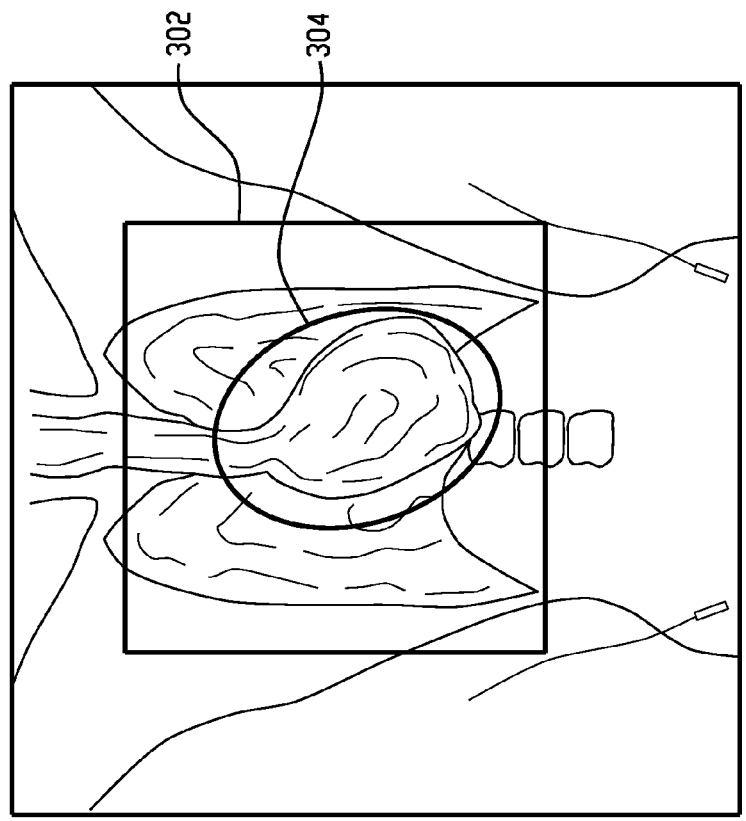
Fig. 3B
Fig. 3A

SCAN PARAMETER POLICY

The following generally relates to imaging an object or subject based on a scan parameter policy and is described with particular application to computed tomography (CT) imaging. However, it is also amenable to other imaging modalities.

According to the literature, medical imaging is the largest controllable source of radiation exposure to the US population, with procedures increasing by 5% to 10% annually, and computed tomography (CT) scans account for about half of the medical radiation incurred by the US population. Furthermore, studies have demonstrated significant variability across vendors and institutions, as well as underutilization of existing CT scanner dose-reduction technologies. Much of this radiation dose variability, and in particular, overdose to an individual patient has been caused by the CT operator through deviation from vendor recommended or institution standard protocols, lack of knowledge/experience in determining appropriate use of radiation dose reduction technologies, and suboptimal selection of scan parameters (e.g., scan range, x-ray technique, gating window, etc.). Furthermore, the incidence of multiple or follow-up CT examinations is also increasing, exposing those patients to a non-insignificant risk associated with cumulative radiation dose.

Unfortunately, the only information available today to the CT scanner operator at the time of scan are numerical dose indices (e.g., CT Volume Dose Index, and Dose-Length Product) that estimate the radiation that will be emitted (exposure) by the CT scanner for a given set of scan parameters prescribed for the current exam. Measures of estimated or absorbed patient, or organ-specific radiation dose as well as measures of estimated risk (e.g., Lifetime Attributable Risk (LAR)) are generally not available at the time of scan. In addition, most registered CT technologists have limited knowledge and/or understanding of medical physics to interpret and/or use these dose indices effectively when planning an examination. This knowledge limitation is further confounded by significant interpatient variation (e.g., resulting from various combinations of body habitus, age, gender, clinical indication, etc.). Moreover, no guidance or training is available to determine patient-specific appropriate use of existing CT scanner dose reduction technologies.

Aspects of the present application address the above-referenced matters and others.

In one aspect, a computing apparatus includes a processor that evaluates at least one scan parameter of a scan protocol selected for scanning a subject with an imaging system based on a corresponding scan parameter policy and generates a signal indicative of whether the scan parameter satisfies the scan parameter policy.

In another aspect, a method includes receiving, by a processor, at least one scan parameters of a scan protocol selected for scanning an object or subject with an imaging system. The method further includes receiving, by the processor, at least one scan parameter policy. The method further includes comparing, via the processor, the at least one scan parameter with the scan parameter policy. The method further includes generating, via the processor, a signal indicative of whether the at least one parameter satisfies the scan parameter policy.

In another aspect, a method includes receiving information indicative of a scan parameter used to scan a patient with an imaging system at a facility and determining from the received information whether the scan parameter satisfies a scan parameter policy for the scan. The method further includes generating a signal indicative of the determination and providing the signal to a reimbursing party. The method further includes receiving a reimbursement for a cost of the imaging procedure based on at least one of an adherence of the scan parameter to the policy or reporting the adherence to the policy to the reimbursing party.

In another aspect, a method includes receiving information indicating whether a scan parameter used to scan a patient with an imaging system at a facility satisfies a scan parameter policy for the scan and determining a reimbursement value based on at least one of an adherence of the scan parameter to the policy or reporting the adherence to the policy to the reimbursing party generating a signal indicative of the determination. The method further includes reimbursing the facility based on the reimbursement value.

In another aspect, a computer readable storage medium containing instructions which, when executed by a computer, cause the computer to perform the acts of: receiving at least one scan parameters of a scan protocol selected for scanning an object or subject with an imaging system, receiving at least one scan parameter policy, comparing the at least one scan parameter with the scan parameter policy, and generating a signal indicative of whether the at least one parameter satisfies the scan parameter policy.

In another aspect, an imaging scan parameter policy generator includes a processor that generates imaging scan parameter policies that are used with imaging systems to determine suitable scan protocol parameters for imaging patients.

The invention may take form in various components and arrangements of components, and in various steps and arrangements of steps. The drawings are only for purposes of illustrating the preferred embodiments and are not to be construed as limiting the invention.

FIGS. 3A and 3B illustrate an example scan parameter change.

Figure 1:
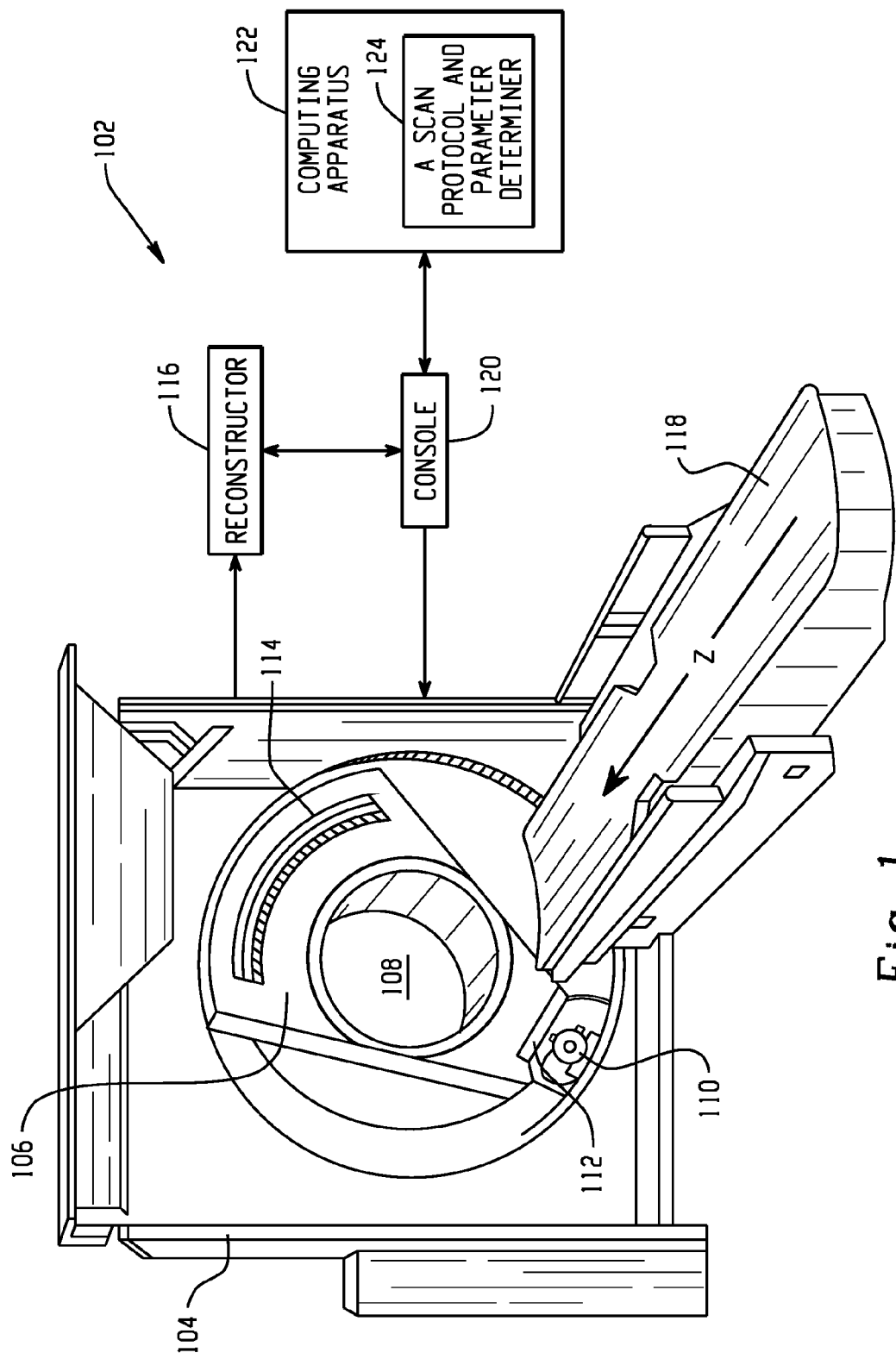
FIG. 1 illustrates a scan protocol and parameter determiner in connection with an imaging system.

FIG. 1 illustrates an imaging system 102 such as a computed tomography (CT) scanner. The imaging system 102 includes a stationary gantry 104 and a rotating gantry 106, which is rotatably supported by the stationary gantry 104. The rotating gantry 106 rotates around an examination region 108 about a longitudinal or z-axis.

A radiation source 110, such as an x-ray tube, is supported by and rotates with the rotating gantry 106, and emits ionizing radiation. A source collimator 112 collimates the radiation to form a generally fan, wedge, or cone shaped radiation that traverses the examination region 108. A radiation sensitive detector array 114 detects photons emitted by the radiation source 110 that traverse the examination region 108 and generates projection data indicative of the detected radiation. The illustrated radiation sensitive detector array 114 includes one or more rows of radiation sensitive photosensor pixels.

A reconstructor 116 reconstructs the projection data and generates volumetric image data indicative of the examination region 108, including any region of an object or subject disposed therein. A support 118, such as a couch, supports the object or subject in the examination region 108. The support 118 is movable along the z-axis in coordination with the rotation of the rotating gantry 106 to facilitate helical, axial, or other desired scanning trajectories.

A general purpose computing system serves as an operator console 120, which includes human readable output devices such as a display and/or printer and input devices such as a keyboard and/or mouse. Software resident on the console 120 allows the operator to control the operation of the system 102, for example, by allowing the operator to select a scan protocol, set scan protocol parameters, initiate, pause and terminate scanning, view and/or manipulate the volumetric image data, and/or otherwise interact with the system 102. In general, the scan parameters correspond to values for settings such as kVp, mAs, number of slices, slice width, pitch, filtering algorithm, scan length, scan field-of-view (FOV), dose reduction algorithm, etc.

A computing apparatus 122 such as a computer, workstation, or the like includes a scan protocol and parameter determiner 124. The scan protocol and parameter determiner 124 provides various scan protocols for selection by an operator of the system 102 and facilitates populating a selected scan protocol with suitable scan parameters. As described in greater detail below, in one instance the scan protocol and parameter determiner 124 initially populates, replaces or suggests/recommends, for at least one default or user defined scan parameter that does not satisfy a scan parameter policy, a scan parameter that satisfies the policy. Sensory feedback such as visual (e.g., color, blinking, graphical icon, etc.), audible (e.g., a buzzer, a beep, a song, etc.), and/or tactile (e.g., a vibrating mouse) feedback can be used to notify the operator of the system 102. As such, the scan protocol and parameter determiner 124 can provide real-time feedback regarding adherence to the scan parameter policy and instructive guidance for setting scan parameters that satisfy the policy.

Although the computing apparatus 122 is shown separate from the system 102 in FIG. 1, it is to be appreciated that at least one of the components of the scan protocol and parameter determiner 124 can be part of the console 120. In addition, the computing apparatus 122 and the console 120 include one or more processors for executing one or more computer executable instructions stored in memory, including instructions for implementing at least a sub-portion of the components of the scan protocol and parameter determiner 124.

Figure 2:
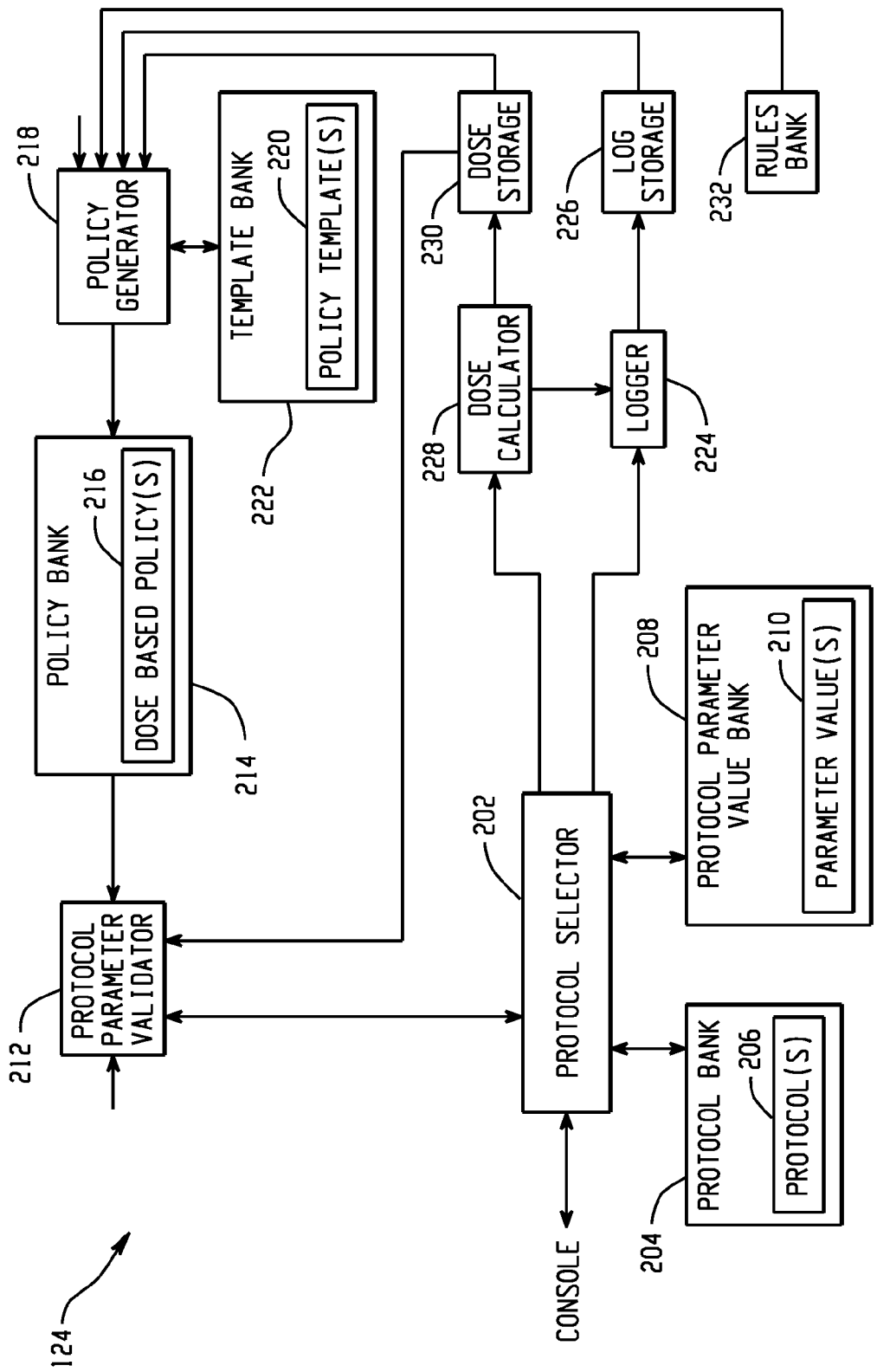
FIG. 2 illustrates an example scan protocol and parameter determiner.

FIG. 2 illustrates an example scan protocol and parameter determiner 124.

A protocol selector 202 provides various scan protocols for selection by the operator. In the illustrated embodiment, a protocol bank 204 stores one or more scan protocols 206, including the provided scan protocols. A protocol parameter value bank 208 stores one or more parameter values 210 for the scan protocols in the protocol bank 204. One or more of the protocols 206 can be vendor, facility, and/or clinician defined. The parameter values 210 for a selected scan protocol 206 may be based on the type of scan (e.g., chest, head, etc.) and/or other information such as patient information, including, but not limited to, patient demographics, pathology, previous scans, future scan (e.g., post radiation therapy), scan of other patients, and/or other information.

A protocol parameter validator 212 validates scan parameter values (also referred to as scan parameters herein) for the selected scan protocol and generates a signal indicative thereof. In the illustrated embodiment, the protocol parameter validator 212 validates the parameters against a predetermined policy. In one instance, parameter validation occurs dynamically, in real-time as parameters are set or defined for the selected scan protocol. As such, protocol parameters can be suggested and/or the protocol can be populated with a set of parameters that satisfy the policy and presented thereafter to the operator. In addition, each time a parameter is set or changed, the protocol parameter validator 212 can validate the scan parameters against the policy. As such, protocol parameter validator 212 can provide information relevant for setting scan parameters for planning an imaging examination or a series of imaging examinations (including follow-up, post-radiation therapy, other future examinations) at the time of the scan. In some instances, such information can be used to guide and/or train the operator with setting appropriated scan parameters based on various objectives such as reducing patient dose, optimizing image quality, etc.

When a default and/or user defined parameter differs from a policy-based parameter, the scan protocol and parameter determiner 124 can variously respond. By way of example, in one embodiment the protocol parameter validator 212 automatically updates parameters that do not satisfy the policy by replacing such parameters with parameters that satisfy the policy. With this embodiment, the protocol selector 202 may require confirmation of the change by authorized personnel prior to permitting the protocol to be used for an imaging procedure. The protocol selector 202 may variously indicate such changes. For example, in one instance the changed parameter is presented in a different color, size, font, etc., which may indicate the change and/or other information such as an urgency level. In another instance, a graphical, textual and/or verbal message indicating the change is presented to the operator. In yet another instance, changes in graphical user interface controls (e.g., text boxes, drop-down menus, buttons, scroll bars, etc.) such as color, shape, and/or other changes are used to indicate, emphasize and/or highlight a scan parameter(s) that does not satisfy one or more policy and/or a replacement scan parameter(s), satisfying a policy, substituted for the scan parameter.

In another embodiment, the protocol parameter validator 212 suggests or recommends replacement parameters that satisfy the policy. In this embodiment, likewise the replacement parameter can be presented in a different color, size, font, etc., a textual and/or verbal message indicating the suggestion can be provided, and/or interface controls can be change to indicate the suggestion. An operator then either accepts or rejects the suggestion. In one instance, a parameter suggestion can only be accepted or rejected by personnel authorized to reject and confirm a policy suggested parameter. Acceptance and/or rejection can be through the console 120 and/or otherwise, for example, via marquee, phone, email, page, text message, instant message, web service, etc.

By way of example, assume that the protocol parameter validator 212 recommends changing a protocol parameter based on a policy. In this case, the operator, if they do not have accept/reject authority, finds personnel who has confirm/reject authority. That personnel logs in to the system and either accepts or rejects the recommendation. In another case, the protocol parameter validator 212 sends a signal to a dispatch system, which executes software that sends a notification (e.g., page, text message, etc.) to the personnel who has accept/reject authority. The dispatch system can be part of the imaging system 100 or a different system.

The notification may simply indicate that personnel is needed to accept/reject a recommended scan parameter value. The notification may also include other relevant information such as the particular parameter, the initial parameter value, the recommended parameter value, patient history, and/or other information. The notification may also include other information. In this particular example, the notified personnel accesses a web based application on a computing device (e.g., a desktop pc, a cell phone, etc.) that allows the personnel to see the protocol, including the initial parameter values and any recommended parameter values, the policy, and/or other information. The personnel can use the web-based application to accept or reject the recommendation.

Other information that may be used to validate parameters, provide recommendations, and/or replace scan parameters includes, but is not limited to, patient state information such as a physiologic state (e.g., heart rate, respiratory rate, blood chemistry, etc.), a physical state (e.g., tired, rested, post-radiation therapy, etc.), an emotional state (e.g., anxious, excited, etc.), and/or other state. Furthermore, radiation dose information such as accumulated dose (an accumulated lifetime radiation dose metric) from performed imaging exams and/or estimates of expected dose for follow up exams, etc. can be used to facilitate validating parameters, providing recommendations, and/or replacing scan parameters. In the context of a radiation dose based policy, the automatic scan parameter change or suggestion may be to lower the x-ray tube voltage to 80 kVp, reduce tube current, shorten the scan length, switch to a prospectively gated technique, activate a tube-current modulation or other dose reducing algorithm, reduce the scan field of view, etc.

It is to be appreciated that the change may be from a default, defined or policy-based parameter to another policy-based parameter. That is, the policy validator 212 may determine a particular default or user-defined parameter does not satisfy the policy and then either change the parameter or suggest a parameter that does satisfy the policy. The change may cause another parameter (default, defined or policy-based parameter), which previously satisfied the policy, to now fail the policy. In this instance, the policy validator 212 will also change or suggest a replacement parameter for this parameter. Where more than one change or suggestion exists and/or a change or suggestion causes another parameter to fail validation, then a set of rules and/or a prioritization can be employed to determine an appropriate parameter change.

A policy bank 214 stores scan parameter policies, including, but not limited to, the policy used to validate the parameters of the selected scan protocol. In the illustrated embodiment, the policy bank 214 includes at least one radiation dose based policy 216. Such a policy may indicate suggested protocol parameter values based on patient dose range or threshold for a particular scan, a series of scans, a patient, a facility, etc. Such a policy may optimize or minimize patient dose for diagnostic quality imaging. An example dose policy is discussed below.

Other suitable policies include, but are not limited to, a contrast medium based policy, an image quality based policy, a policy based on multiple factors such as radiation dose and image quality, and/or other based policies. A contrast medium based policy may indicate an injection rate, an injection to scan time, an injection amount, time between contrast studies, etc. for a particular scan, series of scans, patient, etc. This information may facilitate scanning the patient to generate optimal contrast enhanced images or images during a particular phase from contrast uptake to wash out. An image quality based policy may indicate suggested protocol parameter values based on an image noise threshold. A combination policy weighs (e.g., evenly or unevenly) various criteria (e.g., dose, image noise, etc.).

A policy generator 218 generates scan policies, including, but not limited to one or more policies 216 in the policy bank 214. The illustrated policy generator 218 can generate scan policies based on various input, including, but not limited to, a policy template (e.g., a policy template 220 in a template bank 222), rules (e.g., a rule from a rules bank 232), historical radiation dose information for the patient and/or facility, historical policy adherence for the patient and/or facility, operator input (e.g., patient identification, demographics, etc.), and/or other information. A policy can be generated, modified, deleted, etc. automatically, semi-automatically, and/or by authorized personnel such as a staff member with appropriate user and/or user group permissions.

A dose calculator 228 calculates or estimates patient radiation dose for a patient based on the scan parameters. The calculated dose can be stored in a radiation dose storage 230, which can be local and/or remote memory. The radiation dose information can be stored on an individual scan basis for the patient, aggregated over a time period such as per year, lifetime, etc. for the patient, combined with radiation dose information from one or more other procedures or modalities (e.g., for radiation therapy planning), combined with radiation dose information for another patient(s), for example, to determine radiation dose for a particular facility, an average radiation dose for a procedure for one or more facilities, and/or otherwise. The generated radiation dose information includes the historical radiation dose information used by the policy generator 218 for generating policies such as radiation dose based policies.

The radiation dose information may also be provided to the console 120, which may present the radiation dose in a human readable format as a value, a graphical object, and/or otherwise in a graphical user interface (GUI) or the like on a display. By way of example, the dose information may be presented via a graphical radiation dose policy meter with a color gradient where the color is proportional either to the degree of compliance with one or more radiation dose policies or to the allowable radiation dose relative to one or more specific policies or the total allowable radiation dose according to the radiation dose profile.

By way of additional examples, dose information may be presented in or represented via graphical radiation dose histogram where the radiation dose with the current scan parameters is presented or represented by a position on said histogram, which represents population-based dose statistics for similar procedures. Furthermore, graphical representations of radiation dose reduction alternatives available on the scanner may be provided, with color coding, checkbox, and/or other indicia indicating that a specific technology is available/not available, appropriate/inappropriate and/or enabled/disabled.

The radiation dose can also be used to prospectively estimate and/or regulate dose for subsequent imaging procedures by the same or a different patient. The estimated dose can likewise be presented to the operator of the system. Along with the estimate, other dose estimates based on alternative scan parameters may also be displayed.

A logger 224 generates a log with information about the scan protocol used by the system 102 for an imaging procedure. The generated log may include information such as original scan parameters, scan parameters set by the operator, scan parameters suggested by a policy, actual scan parameters used for the imaging procedure, and/or other information. In the illustrated embodiment, the generated log includes the historical policy adherence information used by the policy generator 218. Additionally or alternatively, the generated log includes the calculated and/or aggregated radiation dose information. The logged information can be used for various purposes such as, but not limited to, quality assurance, training, reimbursement, etc. In the illustrated embodiment, the log is stored in log storage 226, which can be local and/or remote memory.

Monitoring of the log may include analyzing temporal trends of relevant radiation dose parameters as well as comparisons between scanners, departments, scanner operators, clinical indications, institutions, geographies, etc. This may include monitoring the frequency and/or severity of non-compliance with policies, rules, and/or recommendations/actions. Such information may be used by pay-for-performance (P4P), pay-for-reporting (P4R) and/or other systems. By way of example, a P4P service may only reimburse (pay) a healthcare provider (e.g., a healthcare facility, a physician, a medical group, etc.) for imaging system based on adherence to one or more policies. Such payment may be all or nothing, depending on adherence, or a graduated system where reimbursement is proportional to the level of adherence. Such a system may encourage improvement of quality and efficiency for a particular healthcare provider through payment incentives and non-payment disincentives. In contrast, a P4R service may reimburse merely based on reporting adherence. A combination of reporting and adherence may also be used for reimbursement purposes.

It is to be appreciated that the computing apparatus 122, the scan protocol and parameter determiner 124, one or more components thereof, one or more of the policies, the dose information, the log, the rules, the scan protocols, and/or the scan protocol parameters can be individual to a scanner, shared throughout a facility, shared across facilities, etc.

FIGS. 3A and 3B illustrate an example scan parameter change based on a radiation dose policy. In this example, the scan parameters correspond to scan length and scan field-of-view (FOV) defined by a scan planning box overlayed on a scout/pilot image. As noted herein, the parameter can be performed automatically or suggested for a semi-automatic or manual update.

FIG. 3A shows an example user defined cardiac CT angiography scan planning box 302. Note the margin between the user defined scan planning box 302 and a general anatomical region 304 in which the heart is located. This margin may be based on default settings, an operator attempting to ensure that none of the heart is missed, a less than optimal protocol (e.g., an adult protocol for an infant), and/or other reason.

FIG. 3B shows an updated cardiac CT angiography scan planning box 306. Note that the margin between the scan planning box 306 and the region 304 is less than the margin between the original scan planning box 302 and the region 304. As a result, the same cardiac coverage can be obtained while reducing patient dose. Indicia such as indicia 308 can also be displayed to facilitate showing the suggested or automatically made change to the scan planning box.

Figure 4:
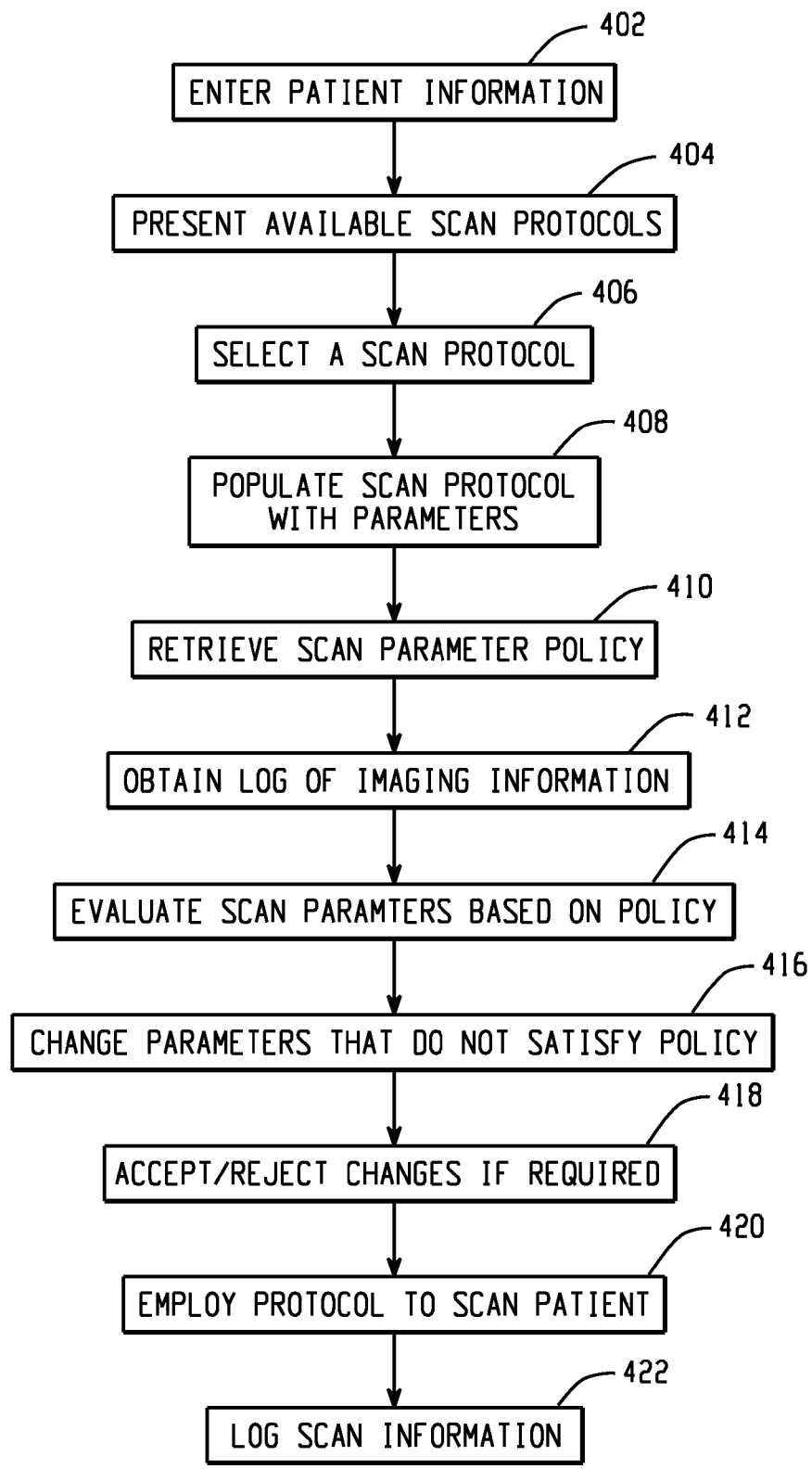
FIG. 4 illustrates a method for automatically populating a scan protocol with scan parameters based on a policy.

FIG. 4 illustrates a method for employing a scan parameter policy to automatically populate scan parameters for a scan protocol.

At 402, patient information for a patient scheduled to be scanned is entered into the console 120.

At 404, available scan protocols are presented for selection.

At 406, a scan protocol of the available scan protocols is selected.

At 408, the scan protocol is populated with default parameters.

At 410, a corresponding scan parameter policy is retrieved.

At 412, logged information relating to previous and/or imaging procedures is obtained, if such information is available. By way of example, for a radiation dose policy, calculated deposited dose for previous imaging procedures, estimated dose for scheduled future imaging procedures, lifetime dose, etc. can be obtained.

At 414, the default scan parameters are evaluated based on the policy and optionally the logged information. For subsequent evaluations of the same protocol, the results of acts 416 and 418 can be taken into account.

At 416, scan parameters that do not satisfy the policy are automatically changed to parameters that satisfy the policy, as described herein. The scan parameters can be changed dynamically, in real-time as they are evaluated, and changes can visually highlighted so that the operator can see what parameters were changed and the parameter values.

At 418, if a change requires authorized personnel acceptance or rejection, the changes are accepted or rejected by authorized personnel.

At 420, the protocol is used to scan the patient.

At 422, scan information is logged. This may include adding the scan parameters (e.g., default, initial, user defined, policy based, etc.) to the above noted log, indicia indicative of adherence to the policy, radiation dose information, and/or other information.

Figure 5:
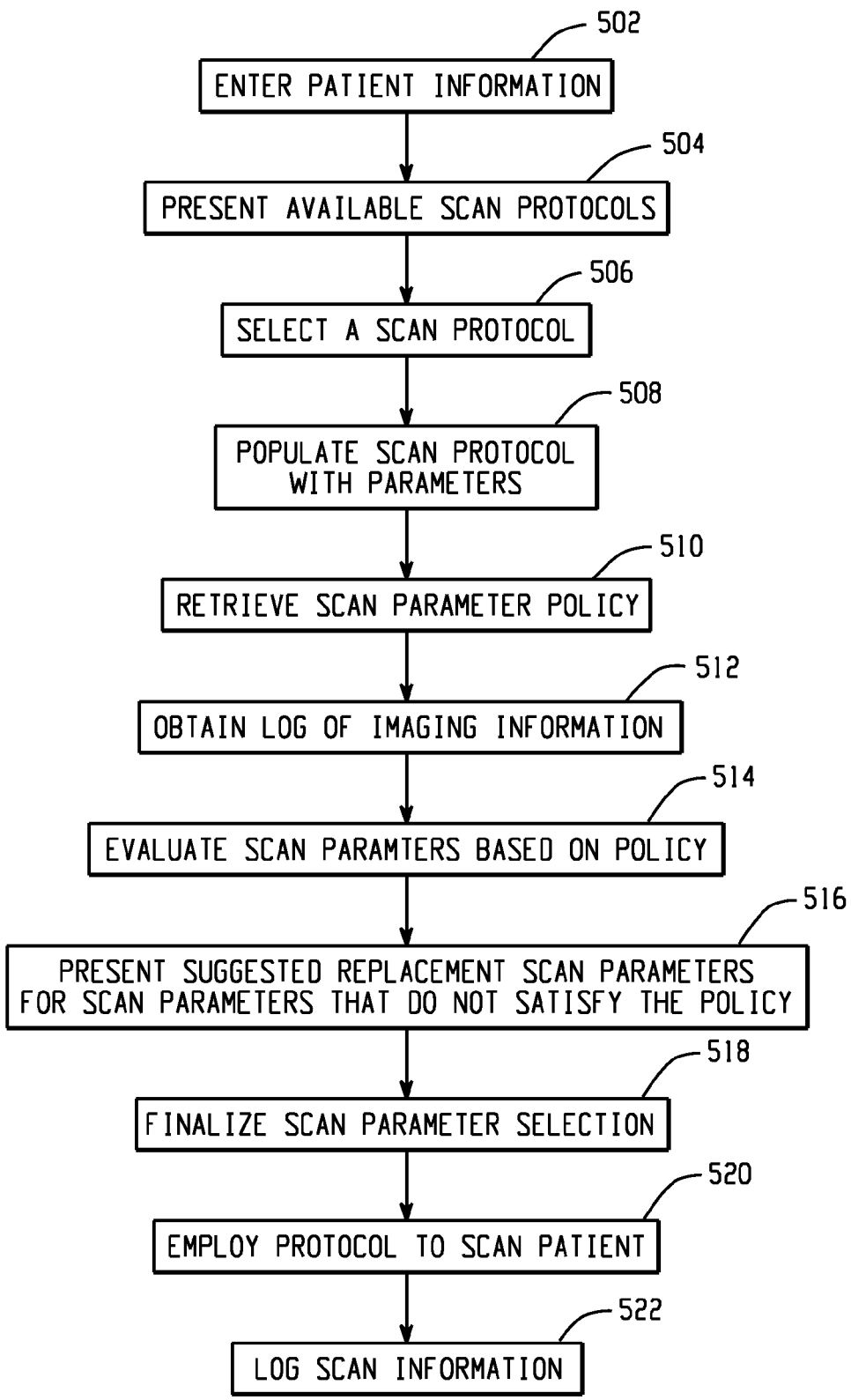
FIG. 5 illustrates a method for suggesting scan parameters for scan parameters that do not satisfy a policy based on the policy.

FIG. 5 illustrates a method for suggesting scan parameters based on a scan parameter policy.

At 502 to 514 corresponds to acts 402 to 414.

At 516, scan parameters are suggested for scan parameters that do not satisfy the policy. As noted herein, this may include highlighting or otherwise emphasizing the scan parameter values that do not satisfy the policy and/or the suggested scan parameter values displayed on the console display or other display.

At 518, the operator can either continue with current scan parameter values or change one or more scan parameter values, for example, in accordance with the suggested scan parameter values.

At 520, the protocol is used to scan the patient.

At 522, scan protocol information is logged.

Figure 6:
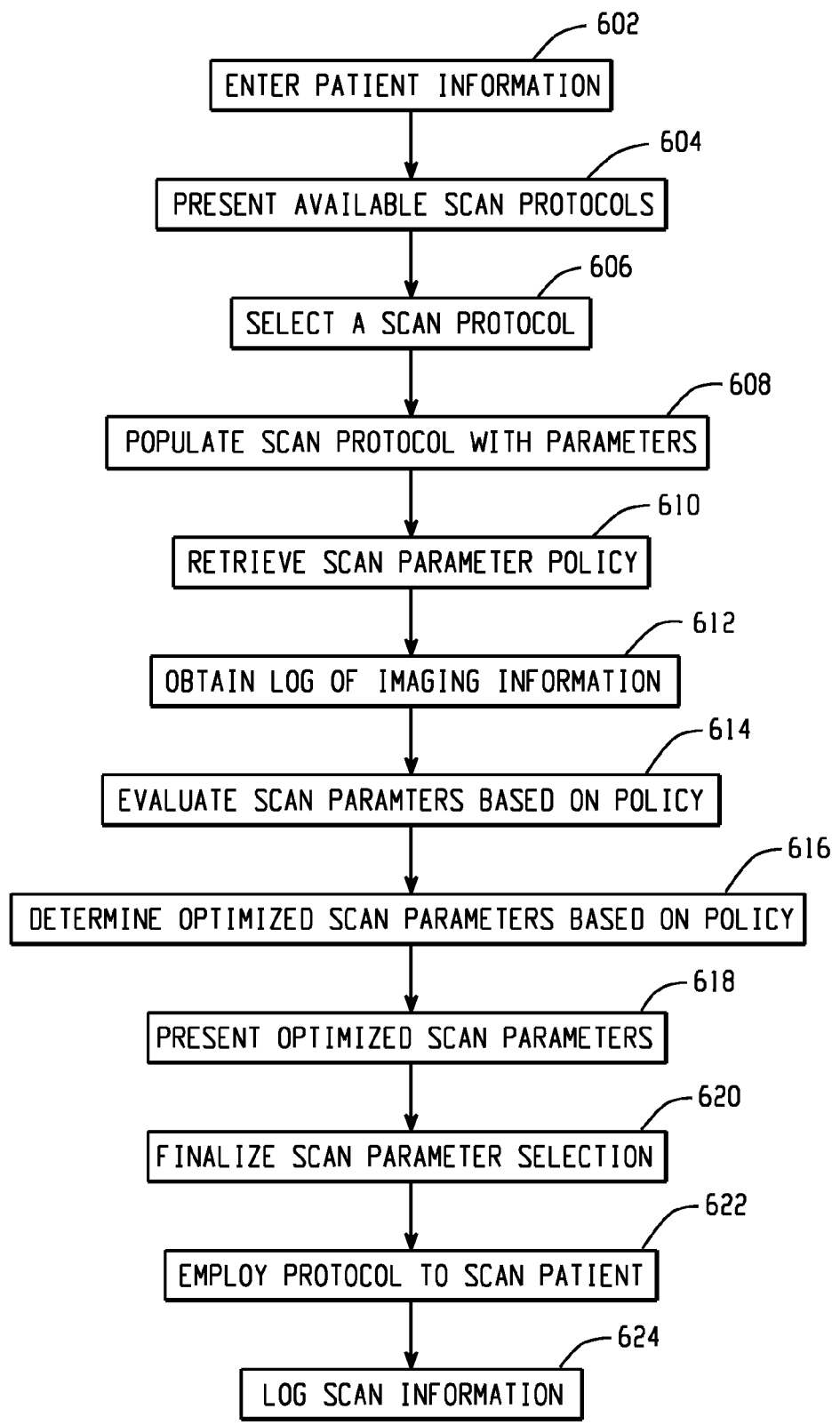
FIG. 6 illustrates a method for suggesting optimized scan parameters based on a policy.

FIG. 6 illustrates a method for optimizing scan parameters based on a scan parameter policy.

At 602 to 614 corresponds to acts 402 to 414.

At 616, optimized replacement scan parameters for scan parameters that satisfy the policy based on the policy are determined based on the policy.

At 618, the optimized replacement scan parameters are presented via a display or otherwise. As such, even if a scan parameter satisfies a policy, a different scan parameter may be better suited for a particular objective. For instance, even if the estimated dose for a set of scan parameters is within a range in a dose policy, a different set of scan parameters may reduce dose without compromising image quality. Such parameters may be presented to the user.

At 620, the operator can either continue with current scan parameter values or change one or more scan parameter values, for example, in accordance with the suggested scan parameter values.

At 622, the protocol is used to scan the patient.

At 624, scan protocol information is logged.

Figure 7:
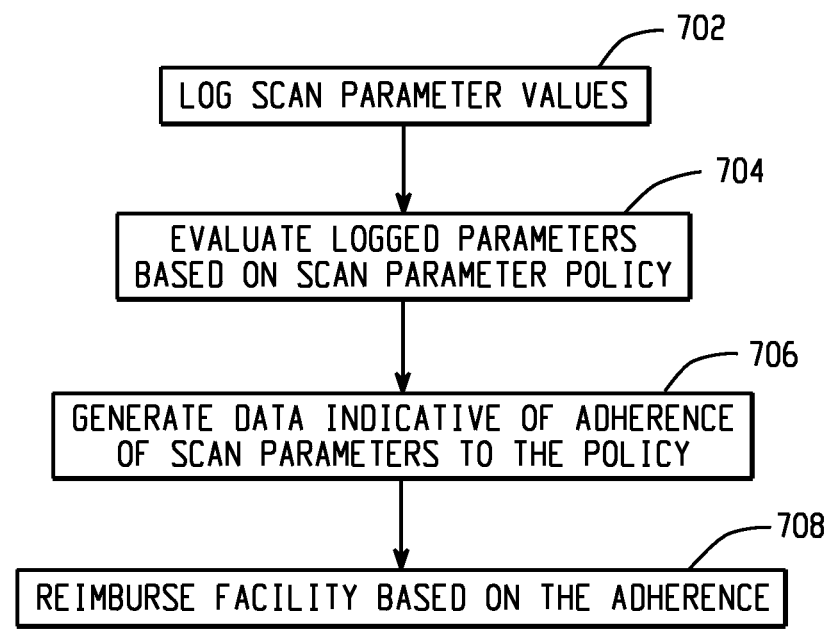
FIG. 7 illustrates a method for reimbursing costs for an imaging procedure based on a policy based on adherence to a policy.

FIG. 7 illustrates a method for reimbursing costs for an imaging procedure based on a policy based on adherence to a policy.

At 702, scan parameter values used to scan a patient at a healthcare facility are logged.

At 704, the logged scan parameter values are checked against a scan parameter policy for the facility.

At 706, information indicative of whether the scan parameter values satisfy the policy is generated. The information is provided to a reimbursing party.

At 708, the reimbursing party reimburses the facility based on the adherence to the policy. In one instance, the reimbursing party reimburses the facility only if all the scan parameters satisfied the policy. In one instance, the reimbursing party partially reimburses the facility based on the degree of adherence to the policy. This can be done on an individual scan based, an individual patient bases, a facility-wide aggregated scan basis, and/or other basis.

Figure 8:
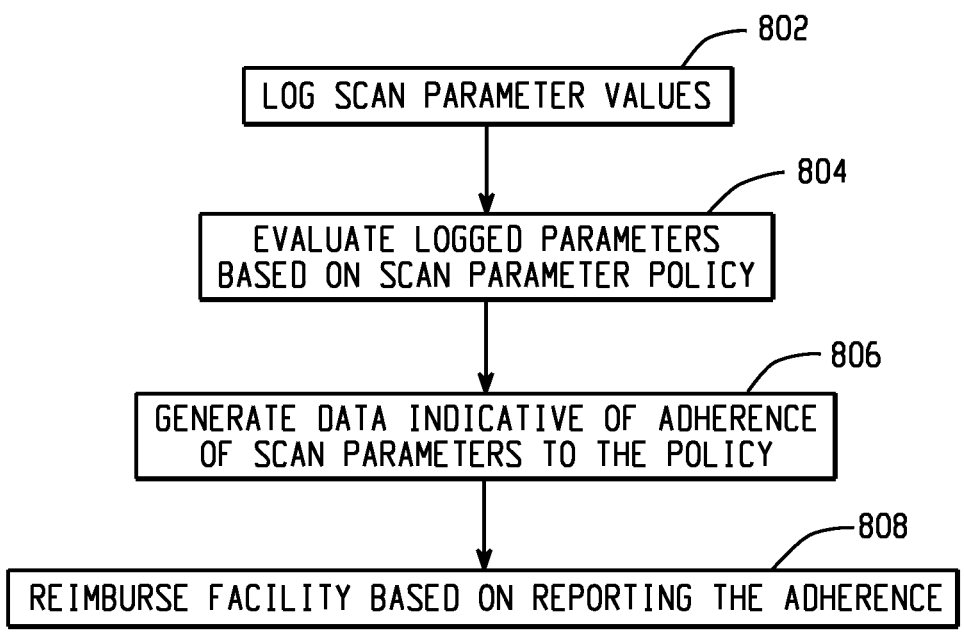
FIG. 8 illustrates a method for reimbursing costs for an imaging procedure based on a policy based on reporting policy adherence information.

FIG. 8 illustrates a method for reimbursing costs for an imaging procedure based on a policy based on reporting policy adherence information.

At 802, scan parameter values used to scan a patient at a healthcare facility are logged.

At 804, the logged scan parameter values are checked against a scan parameter policy for the facility.

At 806, information indicative of whether the scan parameter values satisfy the policy is generated. The information is provided to a reimbursing party.

At 808, the reimbursing party reimburses the facility based on reporting the adherence to the policy.

Figure 9:
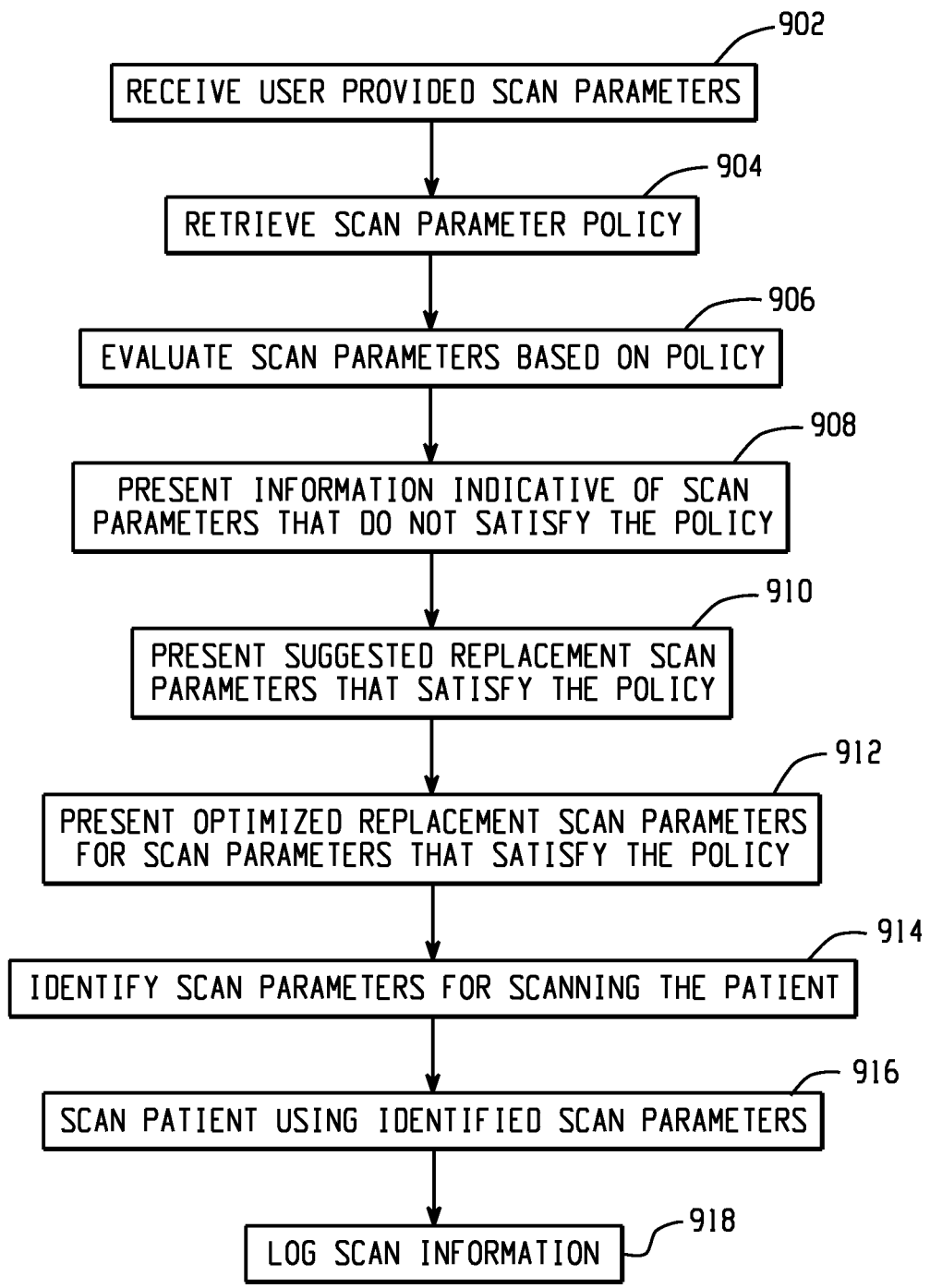
FIG. 9 illustrates a method for guiding or training imaging system operators reimbursing an imaging procedure based on a policy.

FIG. 9 illustrates a method for guiding or training imaging system operators.

At 902, scan parameter values for an imaging procedure are provided via an input device of the console 120 such as a keyboard, mouse, etc. The values may be default values or user specified values.

At 904, a scan parameter policy for the imaging procedure is retrieved.

At 906, the entered scan parameters are checked against the scan parameter policy. The particular policy may take into patient demographics, imaging history and/or other information.

At 908, information indicating that an entered scan parameter does not satisfy the policy is displayed.

At 910, replacement scan parameters for the scan parameters that do not satisfy the policy are displayed.

At 912, optionally, replacement optimized scan parameters for scan parameters that do satisfy the policy are displayed.

At 914, a set of scan parameters for the patient is identified.

At 916, the patient is scanned using the identified set of scan parameters.

At 918, scan information, including the set of scan parameters and adherence to the policy, is logged.

It is to be appreciated that the ordering of the acts in the methods described herein is not limiting. As such, one or more of the acts may occur in a different order, including concurrently with one or more other acts. In addition, one or more of the acts can be omitted and/or one or more other acts can be added. In addition, the acts may be implemented by way of computer readable instructions, which when executed by a computer processor(s), cause the processor(s) to carry out the described acts. In such a case, the instructions are stored in a computer readable storage medium associated with or otherwise accessible to a relevant computer, such as a dedicated workstation, a home computer, a distributed computing system, the console 120, and/or other computer.

The following illustrates a non-limiting example of an ionizing radiation dose based policy, showing multiple data types and sources, multiple rules, user permissions, and revision history.

```
Institution Radiation Dose Policy [XSW.4111.09-221] (Policy.Institution.RadiationDose)
Data Sources
Policy.National.UnitedStates.RaditionDose.2011
Guideline.RadiaitionDose.ACR2007 [www.acr.org]
Guideline.SCCT2009 [www.scct.org]
Patient.ECGInfo
Manufacturer.Scanner.ScannerInfo
Manufacturer.Scanner.Procedure
Manufacturer.Scanner.ScanParameters
Institution.Directory.LDAP
Insitution.RIS
Permissions & Roles
Institution.Directory.LDAP.User.{"johnsmith@institution.org"} = {READ}
Institution.Directory.LDAP.User.{"janesmith@institution.org"} = {READ, WRITE}
Institution.Directory.LDAP.User.{"bobthomas@institution.org"} = {TRANSFER, SYNC}
Institution.Directory.LDAP.UserGroup.{"Physicist"} = {CREATE-MANAGE, QA}
Institution.Directory.LDAP.UserGroup.{"Technologist"} = {USE}
Institution.Directory.LDAP.UserGroup.{"SeniorTechnologist"} = {APPROVE}
Institution.Directory.LDAP.UserGroup.{"Radiologist"} = {USE, APPROVE}
Rules
# CCTA prosepctive gating & heart rate check rule
If {ECGInfo::MeanHR} LE [65 bpm]
     AND {ScanParameters::ScanType} NOT EQ [ProspetiveTrigger]
     AND {Procedure::Name} EQ [CCTA]
     AND {RIS::ClinicalIndication} EQ [CoronaryAssessment]
Then
     <DO ALERT::Operator>
     <DO GUI HIGHLIGHT ScanParameters::ScanType COLOR=RED>
     <DO STATUS DISPLAY "Patient is a candidate for prospective triggering">
     <DO PREVENT::Scan>
End
# Unrestricted emergency department trauma rule
If {RIS::ClinicalIndication} EQ [Trauma]
     AND {ScannerInfo::ScannerLocation} EQ [EmergencyDept]
```

```
Then
      <DO NOT ALERT::Operator>
      <DO NOT PREVENT::Scan>
      <DO OVERRIDE::AllRules>
      <DO LOG::Exceptions>
End
# CCTA scan length exceeds statistically probable scan length
If {Procedure::Name} EQ [CCTA]
      AND {RIS::ClinicalIndication} EQ [CoronaryAssessment]
      AND {ScanParameters::ScanLength} GT
         [MEAN(CCTAPopulationScanLength) +
         2.0*STDEV(Parameters:CCTAPopulationScanLength)]
      OR {ScanParameters::ScanLength} GT
1.2*[Procedure::AutoAnatomyLengthDetect]
Then
      <DO GUI HIGHLIGHT ScanParameters::ScanLength COLOR=RED>
      <DO STATUS DISPLAY "Planned scan length exceeds probably anatomic scan
length. Please verify">
      <DO GUI ADJUST ScanParameters::ScanPlanBox LENGTH=
         [MEAN(CCTAPopulationScanLength) +
         2.0*STDEV(CCTAPopulationScanLength)]>
      <DO GUI HIGHLIGHT ScanParameters::ScanPlanBox COLOR=RED>
      <DO PREVENT::Scan>
End
# Planned dose exceeds ACR practice guidelines for diagnostic reference levels
If {Procedure::Name} EQ [NONCONTRASTBRAIN]
      AND {ScanParameters::CTDIvol} GT [ACR207::DxRefLevel::NonContrastBrain]
Then
      <DO GUI HIGHLIGHT ScanParameters::kVp COLOR=RED>
      <DO GUI HIGHLIGHT ScanParameters::mAs COLOR=RED>
      <DO STATUS DISPLAY "Planned scan parameters result in exposure that exceeds
      ACR
         diagnostic reference level. Please adjust.">
      <DO PREVENT::Scan>
End
Switch {ScanParementers::DoseLengthProduct}
Case: LE [200]
      <DO GUI SET RDPMETER::20% COLOR=GREEN>
Case: GE [950]
      <DO GUI SET RDPMETER::95% COLOR=YELLOW>
      <DO STATUS DISPLAY "Planned scan parameters result in radiation exposure
      approaching radiation dose policy. Please verify or adjust scan parameters.">
      DO LOG::Warning>
Case: GT [1000]
      <DO GUI SET RDPMETER::100% COLOR=RED>
      <DO STATUS DISPLAY "Planned scan parameters result in exposure that exceeds
      radiation dose policy. Please adjust scan parameters or contact supervisor for
      override.">
      <DO PREVENT::Scan>
      <DO NOTIFY::SeniorTechnoligst::SMS>
End
# Policy modification rule
If {UserGroup} EQ [Radiologist] AND Policy.Self EQ [MODIFY]
Then
      <DO NOTIFY::Physicist::Email>
      <DO REQUEST::Physicist::Approval>
End
Revision History
[01/01/2009 12:53:31]
Institution.Directory.LDAP.User.{"billjones@institution.org"} → CREATE
[02/08/2010 18:32:07]
Institution.Directory.LDAP.User.{"sarasmith@institution.org"} → MODIFY
```

Radiation dose policies, such as the example shown above, can be based on variety of data types and data sources. For example, suitable data includes, but are not limited to, patient demographics (e.g., age, gender, height, weight, body-mass index, etc.), patient physiology (e.g., heart rate, heart rate variability, oxygen saturation, etc.), organ radiosensitivity tables (e.g., lung, breast, genitalia, orbits, etc.), organ-specific and/or anatomy conversion coefficient tables (k-factors), scan parameters (e.g., tube current, tube voltage, rotation time, scan length, pitch, field-of-view, collimation, patient centering, etc.), and/or scanner dose reduction technologies (e.g., ECG-triggered tube current modulation, automatic current selection, body habitus-based tube current or tube voltage modulation, including z- or craniocaudal direction, angular or transaxial direction, or combined tube current or voltage modulation, prospective ECG triggering, organ-based dose modulation, dynamic z-collimation, adaptive collimation, wedge/bowtie filters, beam filters, etc.).

Suitable data sources include, but are not limited to, professional society guidelines (ACR, SCCT, AMA, AHA, etc.), industry standards (AAPM, MITA, etc.) and scientific publications, vendor recommendations and default protocols, clinical indication (e.g., chest pain, suspected pulmonary embolism, suspected stroke, risk factors for a particular disease, etc.), clinical context (e.g., trauma, screening, diagnosis, follow-up, etc.), prior exam history (e.g., from HIS/RIS/

EMR/PACS, etc.) and/or cumulative radiation profile (e.g., from HIS/RIS/EMR/PACS, etc.), dose registries (e.g., this exam vs. site history vs. regional/national/worldwide history vs. clinical indication and demographics, etc.), operator characteristics (e.g., name, experience level, past performance, etc.), staff member rights (e.g., permission to create and/or modify policies, permission to grant/revoke approval to scan, permission to modify scan parameters, permission to scan), and/or image quality measures (e.g., noise index, SNR, CNR).

Rules, as shown in the policy example above, may include one or more parameters, a comparison (e.g., less than, greater than, etc.), one or more corresponding thresholds, and at least one action. Rules may be combined using logical operations (e.g., and, or, not, xor, etc.) and/or another rule(s) (e.g., 8 of 10 rules must be satisfied, etc.). Rules may be prioritized (e.g., it must be followed, or it may be ranked relative to other rules) and/or may be ordered (e.g., must meet Rule 1 before Rule 2, etc.). Conflicts between one or more rules may be managed during rule generation (i.e., during radiation dose policy creation/management). A general construct for a rule is shown below.

```
if {parameter} {comparison} {threshold}
then
    {action}
else
    {other action}
end
switch {parameter}
case: {comparison} {threshold}
    {action}
case: {comparison} {threshold}
    {other action}
case: {comparison} {threshold}
    {other action}
otherwise:
    {other action}
end
```

For the rules, parameters (e.g., absolute or relative continuous, categorical, binary, etc.) and/or thresholds (e.g., continuous fuzzy or absolute, categorical, binary, absolute, or relative) can be used. Suitable thresholds include, but are not limited to, thresholds where appropriate dose levels can be determined based on clinical indication, prescribed CT procedure, patient-specific demographic and/or physiologic information. Thresholds may also be set with local hospital and/or department guidelines by senior technologists, physicians, and/or medical physicists, with regional or national quality and regulatory policies/guideline, and/or by referencing registry-derived actual population dose data from similar population distributions (e.g., exceeding 1 standard deviation relative to comparative patient/scan/indication) at a department, site, regional, or international level. Thresholds may take into account anatomy being scanned and corresponding radiosensitivity of scanned organs and historical patient-specific cumulative radiation exposure levels derived from EMR, HIS, RIS, and PACS, and/or other thresholds.

For the rules, actions may be targeted to either the people (e.g., the operator) or the CT system (e.g., automatic update of scan parameters). Actions may include various levels such as "no action" (i.e., rule satisfied), "no action required" (i.e., rule violated, but only record violation), "recommend action" (i.e., operator may further minimize dose, but it is not required to do so), "immediate action required to commence scan" (i.e., operator must adjust scan parameters and/or get supervisor sign off prior to commencing scan; scanner will not allow or will actively prevent continuation if rule is not satisfied), etc.

Exceeding dose thresholds may have varying degrees of "consequence" relative to clinical context including "none" for trauma to "complete prevention of scanning" until appropriate changes have been made for pediatrics and/or screening. If CT scanner dose reduction technologies are available and appropriate, but have not been selected or properly configured by technologist, the CT system can automatically change one or more parameters relative to said policies, and optionally provide feedback/information to educate the user. If a policy allows a user to exceed one or more parameter thresholds, the system can provide a prompt to log reason, or require $2^{nd}$ level approval from senior technologist and/or resident physician/physicist for exceeding recommend threshold relative to clinical indication and patient-specific parameters Radiation dose policies may be combined and/or nested to create meta-policies with conflicts between one or more policies managed during policy creation and/or management. Radiation dose policies may be physically stored locally on a specific CT scanner console, on a local area and/or remote network devices, or in any combination. In this way, radiation dose profiles may be downloadable and synchronized across scanner and/or institutions. These policies can exist in proprietary or open source document object models (e.g., DICOM, XML, HL7) and transferred via standard protocols (e.g., HTTP, FTP, SOAP, etc.). Furthermore, radiation dose policies may be managed locally or via network/web service (SMS, text, PDA, etc).

The radiation dose policy system can optionally be linked into image quality (IQ) measures, such as noise index, to ensure that IQ and dose-reduction are balanced within a radiation dose policy. Furthermore, the system can also prevent underexposure ("under dosing") to ensure necessary diagnostic IQ and minimize the potential for repeat scanning. Moreover, the radiation dose policy system can link to offline databases capturing learned physician reading/IQ preferences to set preference-based dose reduction parameter thresholds.

Applications include, but are not limited to, a CT scanner as described herein. Other applications include, but are not limited to, other imaging modalities that use ionizing radiation (e.g., x-ray, fluoroscopy, etc).

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A computing apparatus, comprising:
   a processor that evaluates at least one scan parameter of a scan protocol selected for scanning a subject with an imaging system based on a corresponding scan parameter policy and generates a signal indicative of whether the scan parameter satisfies the scan parameter policy; and
   wherein the scan parameter policy includes at least one rule which compares the at least one scan parameter to at least one predetermined threshold value, and includes at least one action performed based on the comparison.

2. The apparatus of claim 1, wherein the policy includes at least one of a radiation dose policy corresponding to ionizing radiation exposure, a contrast agent policy, or an image quality policy.

3. The apparatus of claim 1, wherein the processor prevents the scan in response to the scan parameter not satisfying the at least one predetermined threshold value and the at least one action performed includes preventing the scan.

4. The apparatus of claim 1, wherein the processor displays, based on the policy, a suggested replacement scan parameter that satisfies the policy in response to the scan parameter not satisfying the policy, and the at least one action includes providing the suggested replacement scan parameter.

5. The apparatus of claim 4, wherein at least one of the scan parameter or the replacement scan parameter is graphically presented to indicate compliance with the policy.

6. The apparatus of claim 4, wherein the replacement scan parameter is used to guide or train an operator of the system.

7. The apparatus of claim 1, wherein the processor displays, based on the policy, a suggested optimized replacement scan parameter for a scan parameter that satisfies the policy based on predetermined optimization criteria.

8. The apparatus of claim 1, wherein the processor displays, based on the policy, one or more alternative replacement scan parameters that satisfy the policy.

9. The apparatus of claim 1, wherein the processor automatically replaces, based on the policy, the scan parameter in response to the scan parameter not satisfying the policy with a replacement scan parameter that satisfies the policy.

10. The apparatus of claim 1, further comprising:
a dose calculator that generates and displays a radiation dose value indicative of a radiation dose for the subject based at least in part on the scan parameter.

11. The apparatus of claim 10, wherein the radiation dose value is displayed in connection with a radiation dose histogram, which shows radiation dose values representing population based dose statistics for similar imaging procedures, at a corresponding location of the radiation dose histogram.

12. The apparatus of claim 10, wherein the value is used to generate an accumulated lifetime radiation dose metric for the subject.

13. The apparatus of claim 10, wherein the radiation dose value is presented in a graphical dose policy meter.

14. The apparatus of claim 13, wherein the dose policy meter includes a color gradient in which a color of the radiation dose value is proportional to a degree of compliance with a dose metric of the scan parameter policy.

15. The apparatus of claim 13, wherein the dose policy meter includes a color gradient in which a color of the radiation dose value is proportional to a predetermined allowable lifetime dose exposure for the subject.

16. The apparatus of claim 10, wherein the value is used to estimate a radiation dose for a subsequent scan of the subject or a different subject.

17. The apparatus of claim 10, wherein the scan parameter is validated based on at least one of the radiation dose for the scan, an accumulated radiation dose, or an estimated radiation dose.

18. The apparatus of claim 10, wherein the processor suggests alternative sets of scan parameters that reduce deposited dose based on the policy.

19. The apparatus of claim 18, wherein each of the alternative sets of scan parameters is graphically presented with indicia that indicates a dose reduction value relative to the other of the alternative sets of scan parameters.

20. The apparatus of claim 18, wherein each of the alternative sets of scan parameters is presented with indicia that indicates whether the corresponding set of scan parameters is available for selection for scanning the subject.

21. The apparatus of claim 18, wherein each of the alternative sets of scan parameters is presented with indicia that indicates whether the corresponding set of scan parameters is suitable for scanning the subject.

22. The apparatus of claim 1, further comprising:
a logger that generates a log of scan parameters used to scan the subject.

23. The apparatus of claim 22, wherein the log includes indicia indicating whether the scan parameter satisfied the policy.

24. The apparatus of claim 22, wherein the log is provided to a pay for performance party that uses the log to reimburse the cost of the scan based on adherence to the policy.

25. The apparatus of claim 22, wherein the log is provided to a pay for reporting party that uses the log to reimburse the cost of the scan based on reporting of adherence to the policy.

26. The apparatus of claim 1, further comprising:
a policy generator that generates scan parameter policies stored in a policy bank, including the corresponding scan parameter policy.

27. The apparatus of claim 26, wherein the policy generator generates at least one policy based on one or more of a predetermined radiation dose, contrast agent or image quality metric.

28. The apparatus of claim 26, wherein the policy generator generates at least one policy based on one or more of a policy template or a policy rule.

29. A method, comprising:
receiving, by a processor, at least one scan parameter of a scan protocol selected for scanning an object or subject with an imaging system;
receiving, by the processor, at least one scan parameter policy from a policy bank and the at least one scan parameter policy includes at least one rule;
comparing, via the processor, the at least one scan parameter with the scan parameter policy using the at least one rule which compares the at least one scan parameter to at least one predetermined threshold, and the at least one rule includes at least one action performed based on the comparison; and
generating, via the processor, a signal indicative of the at least one action performed.

30. The method of claim 29, wherein the at least one action performed includes preventing the scan.

31. The method of claim 29, wherein the at least one action performed includes automatically replacing that scan parameter with a scan parameter that satisfies the policy.

32. The method of claim 31, wherein the at least one action includes presenting the replaced scan parameter for acceptance or rejection.

33. The method of claim 29, wherein the at least one action includes presenting a suggested replacement scan parameter if the scan parameter does not satisfy the policy.

34. The method of claim 33, wherein the at least one action includes graphically presenting the suggested replacement parameter respectively with a dose reduction estimate.

35. The method of claim 33, wherein the at least one action includes graphically presenting the suggested replacement parameter with indicia that indicates whether the parameter is available for selection for scanning the subject.

36. The method of claim 33, wherein the at least one action includes graphically presenting the suggested replacement parameter with indicia that indicates whether the parameter is suitable for scanning the subject.

37. The method of claim 33, wherein the at least one action includes:
receiving an input invoking replacement of the scan parameter with the suggested replacement scan parameter.

38. The method of claim 29, wherein the at least one action includes:
presenting one or more alternative replacement scan parameters for the scan parameter if the scan parameter satisfies the policy.

39. The method of claim 38, wherein the one or more alternative replacement scan parameters facilitate reducing patient dose, and wherein the at least one action includes presenting an estimated dose for each of the alternative replacement scan parameters.

40. The method of claim 39, wherein the at least one action includes presenting indicia indicating whether an alternative replacement scan parameter is available for selection for scanning the subject.

41. The method of claim 39, wherein the at least one action includes presenting indicia indicating whether the one or more alternative replacement scan parameters are suitable for scanning the subject.

42. The method of claim 29, wherein the at least one action includes:
determining an estimated radiation dose value based on the scan parameter prior to the scan; and
presenting the dose value.

43. The method of claim 29, wherein the at least one action includes:
determining a radiation dose value for a scan of the scan protocol based on the scan parameters after the scan; and
presenting the radiation dose value.

44. The method of claim 43, wherein the radiation dose value is displayed in connection with a radiation dose histogram, showing radiation dose values representing population based dose statistics for similar imaging procedures, at a corresponding location of the radiation dose histogram.

45. The method of claim 43, wherein the radiation dose value is presented in a graphical dose policy meter.

46. The method of claim 45, wherein the dose policy meter includes a color gradient in which a color of the radiation dose value is proportional to a degree of compliance with a dose metric of the scan parameter policy.

47. The method of claim 45, wherein the dose policy meter includes a color gradient in which a color of the radiation dose value is proportional to a predetermined allowable lifetime dose exposure for the subject.

48. The method of claim 29, wherein the at least one action includes:
generating a logging that includes the scan parameter used to scan the subject, wherein the log includes indicia indicating whether the scan parameter satisfied the policy.

49. The method of claim 48, wherein the log is provided to a pay for performance party that uses the log to reimburse the cost of the scan based on adherence to the scan parameter policy.

50. The method of claim 48, wherein the log is provided to a pay for reporting party that uses the log to reimburse the cost of the scan based on reporting of adherence to the policy.

51. The method of claim 29, further comprising:
generating the at least one scan parameter policy which is stored in the policy bank of a computing apparatus.

52. The method of claim 51, wherein the at least one scan parameter policy is generated with rules based on one or more of a predetermined radiation dose, contrast agent or image quality metric.

53. The method of claim 51, wherein the policy is generated based on one or more of a policy template or a policy rule and stored in the policy bank.

54. A method, comprising:
receiving information indicative of a scan parameter used to scan a patient with an imaging system at a facility;
determining from the received information whether the scan parameter satisfies a scan parameter policy for the scan and the scan parameter policy is retrieved from a policy bank of a computing apparatus, and the scan parameter policy includes at least one rule which compares the scan parameter with a threshold and the at least one rule includes at least one action to be performed based on the comparison;
generating a signal indicative of the determination which includes the at least one action to be performed;
performing the at least one action to be performed which includes providing the signal to a reimbursing party which includes whether the scan parameter satisfies the scan parameter policy; and
receiving a reimbursement for a cost of the imaging procedure based on at least one of an adherence of the scan parameter to the scan parameter policy or reporting the adherence to the policy to the reimbursing party.

55. A method, comprising:
receiving information indicating whether a scan parameter used to scan a patient with an imaging system at a facility satisfies a scan parameter policy for the scan, wherein the scan parameter policy includes at least one rule which compares the scan parameter to a threshold and performs at least one action based on the comparison which includes sending the information indicating whether the scan parameter used to scan a patient with an imaging system at the facility satisfies the scan parameter policy for the scan;
determining a reimbursement value based on at least one of an adherence of the scan parameter to the policy or reporting the adherence to the scan parameter policy to a reimbursing party;
generating a signal indicative of the determination that includes the reimbursement value and an indicator of the scan parameter adherence to the scan parameter policy; and
reimbursing the facility based on the reimbursement value and adherence of the scan parameter to the scan parameter policy.

56. A non-transitory computer readable storage medium containing instructions which, when executed by a computer, cause the computer to perform the acts of:
receiving at least one scan parameter of a scan protocol selected for scanning an object or subject with an imaging system;
receiving at least one scan parameter policy from a policy bank, and the at least one scan parameter policy includes at least one rule;
comparing the at least one scan parameter with the scan parameter policy which includes evaluating the at least one rule that compares the at least one scan parameter with a threshold and the at least one rule includes at least one action to be performed based on the evaluation; and
generating a signal indicative of whether the at least one parameter satisfies the scan parameter policy and the signal indicates the at least one action to be performed based on the evaluation of the rule.

57. An imaging scan parameter policy generator, comprising:
- a processor that generates a plurality of imaging scan parameter policies that are used with imaging systems to determine suitable scan protocol parameters for imaging patients, and each imaging scan parameter policy includes at least one rule which compares at least one imaging scan parameter with a threshold, and the at least one rule includes at least one action performed based on the comparison.

58. The policy generator of claim 57, wherein the processor generates a policy with rules based at least on one or more of a predetermined dose, contrast agent or image quality metric.

59. The policy generator of claim 57, wherein the processor generates at least one patient specific scan parameter policy.

60. The policy generator of claim 59, wherein the patient specific scan parameter policy is generated based on historical imaging information of the patient.

61. The policy generator of claim 57, wherein at least one of the scan parameter policies is editable only by authorized personnel with policy editing permission which modify the at least one rule.

62. The policy generator of claim 57, wherein the scan parameter policies are shared across multiple imaging systems.

63. The policy generator of claim 57, wherein the scan parameter policy is applied to a default or user defined set of protocol parameters and the at least one action includes at least one of: a generated signal that the default or user defined set of protocol parameters satisfies the policy in response to evaluating the at least one rule with the default or user defined set of protocol parameters within the threshold, or a generated signal that the default or user defined set of protocol parameters does not satisfy the policy in response to evaluating the at least one rule with the default or user defined set of protocol parameters exceeding the threshold.

* * * * *